(12) United States Patent
Lecat

(10) Patent No.: US 8,287,283 B2
(45) Date of Patent: Oct. 16, 2012

(54) ARRANGEMENT FOR AUSCULTATION TRAINING

(76) Inventor: Paul Jacques Charles Lecat, Tallmadge, OH (US)

( * ) Notice: Subject to any disclaimer, the term of this patent is extended or adjusted under 35 U.S.C. 154(b) by 1054 days.

(21) Appl. No.: 11/935,468

(22) Filed: Nov. 6, 2007

(65) Prior Publication Data

US 2009/0117526 A1    May 7, 2009

(51) Int. Cl.
G09B 23/28    (2006.01)
A61B 5/02     (2006.01)

(52) U.S. Cl. ........................ 434/266; 600/528

(58) Field of Classification Search .................. 434/266; 381/67; 600/528, 586; 181/131, 137; D24/134
See application file for complete search history.

(56) References Cited

U.S. PATENT DOCUMENTS

| | | | |
|---|---|---|---|
| 4,770,189 | A | 9/1988 | Shyu |
| 6,220,866 | B1 | 4/2001 | Amend et al. |
| 7,115,102 | B2 | 10/2006 | Abbruscato |
| 7,209,796 | B2 | 4/2007 | McKinney et al. |
| 2003/0002685 | A1 * | 1/2003 | Werblud .................... 381/67 |
| 2004/0076303 | A1 | 4/2004 | Vyshedsky et al. |
| 2004/0157612 | A1 | 8/2004 | Kim |
| 2005/0048455 | A1 | 3/2005 | Hayamizu et al. |
| 2007/0178430 | A1 | 8/2007 | Lecat |

FOREIGN PATENT DOCUMENTS

KR    10-2006-0025301 A    3/2006

OTHER PUBLICATIONS

Supplementary European Search Report and Written Opinion, dated Jan. 27, 2011, European Patent Office, EP08847944.9.
International Preliminary Report on Patentability, dated Mar. 15, 2011, World Intellectual Property Organization, PCT/US2008/082417.
International Search Report, dated Jul. 14, 2009, Korean Intellectual Property Office, PCT/US2008/082417.

* cited by examiner

*Primary Examiner* — Kathleen Mosser
(74) *Attorney, Agent, or Firm* — Roger D. Emerson, Esq.; Ray C. Meiers, Esq.; Emerson Thomson Bennett LLC

(57) ABSTRACT

A cap composition that can mechanically attach to a stethoscope headpiece, the cap composition having a cap; a cap element having a design that includes a shape and characteristic dimensions that enable the cap to mechanically attach to a stethoscope headpiece; and a speaker attached to and positioned on or at least partially within the cap, such that when the cap is attached to the stethoscope headpiece, the speaker is either touching or proximate to the stethoscope diaphragm such that a sound or signal emitted by the speaker can cause the stethoscope diaphragm to vibrate.

16 Claims, 5 Drawing Sheets

ARRANGEMENT FOR AUSCULTATION TRAINING

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of Invention

Embodiments are directed to compositions and methods relating to auscultation training.

2. Description of the Related Art

Auscultation is the act of listening to sounds within the body as a method of diagnosis. A stethoscope is an example of an auscultation device that is used in the medical field to listen to internal sounds in the human body, such as for example heart sounds, breathing (breath sounds), intestinal noises, and blood flow in arteries and veins. Acoustic stethoscopes operate on the transmission of sound from a headpiece, via air-filled hollow tubes, to a listener's ears. The headpiece may include a diaphragm that can be placed against a human body for sensing sound. Body sounds vibrate the diaphragm, creating acoustic pressure waves that travel to the tubing to the listener's ears.

Using a stethoscope or other auscultation device to diagnosis a patient requires training in detecting and identifying the abnormal auditory findings. Standardized patients are a valuable training tool in Medical Education and have been extensively researched. Though standardized patients give students one-on-one interaction with real patients, most standardized patients do not have abnormal physical findings. As a result, simulators and mannequins are often used to train or test students on auscultation devices, such as stethoscopes. Auscultation training mannequins may include a sound generating device embedded within the body of the mannequin to produce sounds consistent with an abnormal physical condition, which students must detect and identify.

BRIEF SUMMARY OF THE INVENTION

The present application is directed to one or more arrangements and methods for auscultation training. In particular the invention relates to an arrangement that transmits audio signals to an auscultation device. An embodiment of the arrangement is useful for medical simulation.

An embodiment is directed to a cap composition that can mechanically attach to a stethoscope headpiece, the cap composition having a cap; a cap element having a design that includes a shape and characteristic dimensions that enable the cap to mechanically attach to a stethoscope headpiece; and a speaker attached to and positioned on or at least partially within the cap, such that when the cap is attached to the stethoscope headpiece, the speaker is either touching or proximate to the stethoscope diaphragm such that a sound or signal emitted by the speaker can cause the stethoscope diaphragm to vibrate.

An embodiment is directed to an arrangement for auscultation training, the arrangement having a signal generator capable of generating an audio signal representing at least one sound; a transmitter that transmits the audio signal; an auscultation device remote from the transmitter, the auscultation device comprising: a receiver for receiving the audio signal transmitted by the transmitter; a speaker for communicating the audio signal received by the receiver; and a recording device that makes a record of the sound or signal emitted by the speaker.

Further aspects and concepts will become apparent to those skilled in the art after considering the following description and appended claims in conjunction with the accompanying drawings.

DETAILED DESCRIPTION OF THE INVENTION

An arrangement for auscultation training and related methods are presented. While some embodiments illustrated and described herein are presented in the context of medical diagnosis using a stethoscope including an FM radio receiver for receiving audio signals from a remote FM transmitter associated with all audio device, those skilled in the art will readily appreciate that the general embodiments may be used and configured in other ways. For example, the embodiments, though referred to as for auscultation training, may be used outside of the medical profession for training in the diagnosis of problems with equipment or engines or anything that may be diagnosed by detecting and identifying a characteristic sound generated by the subject article. In addition, the remote transmitter and receiver need not necessarily be an FM radio transmitter and receiver, but may utilize any suitable wireless technology capable of transmitting an audio signal, such as for example, AM radio frequency, Bluetooth, ZigBee, WiFi, and other technologies. Furthermore, the device used to detect the sound on the person or thing being diagnosed need not necessarily be a stethoscope, but can be any suitable auscultation device or sound detecting device.

While various aspects and concepts of the invention are described and illustrated herein as embodied in combination in exemplary embodiments, these various aspects and concepts may be realized in many alternative embodiments, either individually or in various combinations and sub-combinations thereof. Unless expressly excluded herein all such combinations and sub-combinations are intended to be within the scope of the present invention. Still further, while various alternative embodiments as to the various aspects and features of the invention, such as alternative materials, structures, configurations, methods, devices, software, hardware, control logic and so on may be described herein, such descriptions are not intended to be a complete or exhaustive list of available alternative embodiments, whether presently known or identified herein as conventional or standard or later developed. Those skilled in the art may readily adopt one or more of the aspects, concepts or features of the invention into additional embodiments within the scope of the present invention even if such embodiments are not expressly disclosed herein. Additionally, even-though some features, concepts or aspects of the invention may be described herein as being a preferred arrangement or method, such description is not intended to suggest that such feature is required or necessary unless expressly so stated. Still further, exemplary or representative values and ranges may be included to assist in understanding the present invention however, such values and ranges are not to be construed in a limiting sense and are intended to be critical values or ranges only if so expressly stated.

Figure 1:
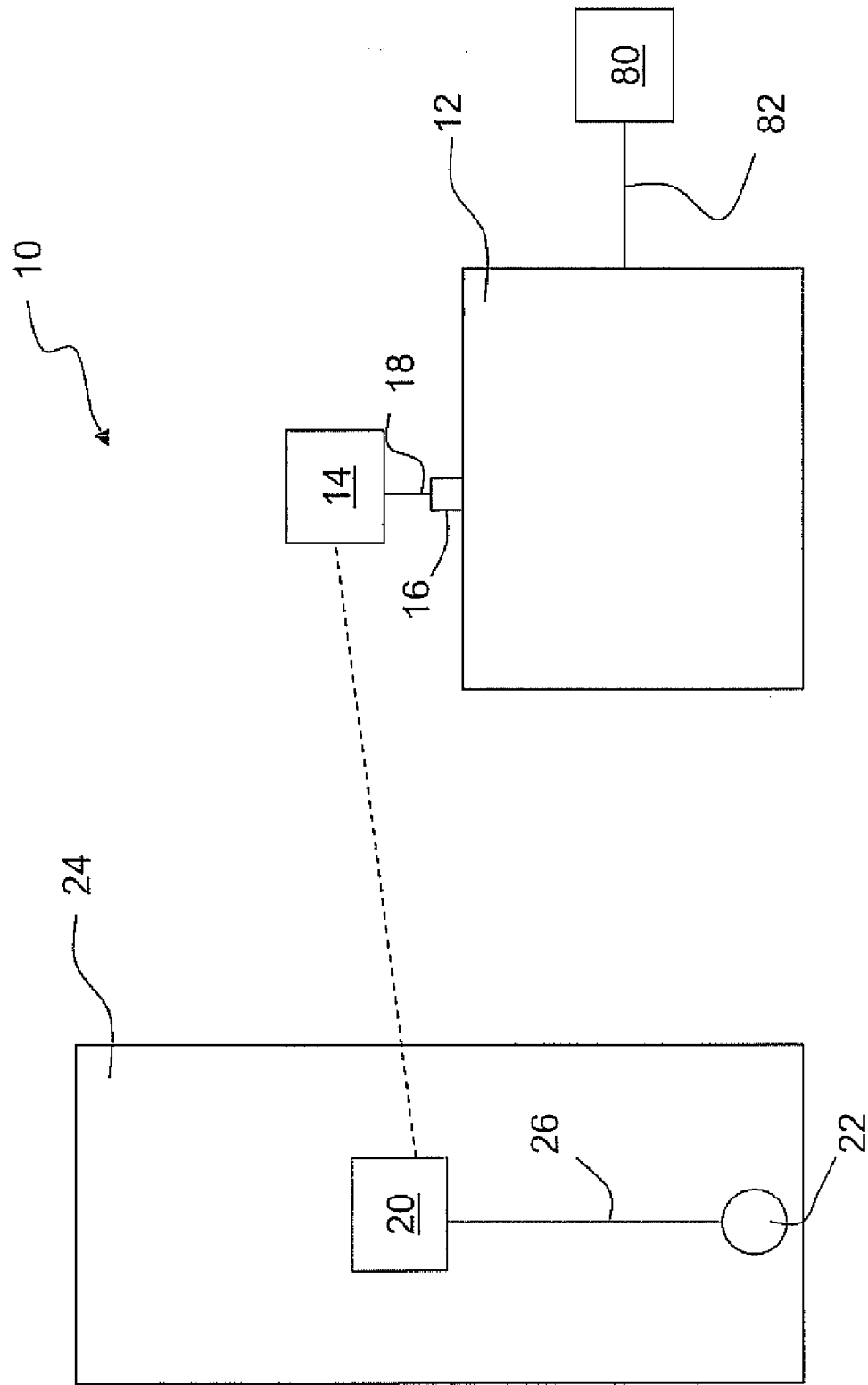
FIG. 1 is schematic illustration of an embodiment of an exemplary arrangement for auscultation training.

FIG. 1 schematically illustrates an embodiment of an arrangement for auscultation training. Arrangement 10 may include device 12 capable of generating an audio signal and wireless transmitter 14 associated with device 12. Device 12 is capable of generating an audio signal, and may be any of a wide variety of devices, such as for example, a compact disc player, a cassette player, a digital audio player (e.g. MP3 player, IPod player from Apple Computers), a Personal Digital Assistant (PDA), a computer, or other suitable device. Device 12 may have a wide variety of sounds stored in memory as audio signals, thus creating a large number of sounds that may be transmitted as audio signals at the choice of a user for very specific teaching, testing, or research.

Wireless transmitter 14 may be integrated with device 12 or may be in circuit communication with the device. In an embodiment, device 12 may include output 16 such as for example, a USB port, a headphone jack or other similar output, and wireless transmitter 14 may connect to output 16 by, for example, an electrical wire and connection 18, such that device 12 may communicate an audio signal to transmitter 14.

Arrangement 10 may also include receiver 20 remote from transmitter 14 and adapted to receive a wireless audio signal from transmitter 14. Receiver 20 and transmitter 14 may utilize any suitable wireless technology capable of communicating an audio signal from a transmitter to a receiver. For example, transmitter 14 may transmit using FM radio, AM radio, Bluetooth, ZigBee, WiFi, or other suitable technologies.

Arrangement 10 may also include audio output device 22, such as a speaker for example, capable of communicating the one or more sounds represented in an audio signal to an end user. Receiver 20 and output device 22 may be attached to or integrated in auscultation device 24, such as for example, a stethoscope. Audio output device 22 may be integral with receiver 20 or in communication with receiver 20, such as for example, via electrical wire and connection 26.

Figure 2:
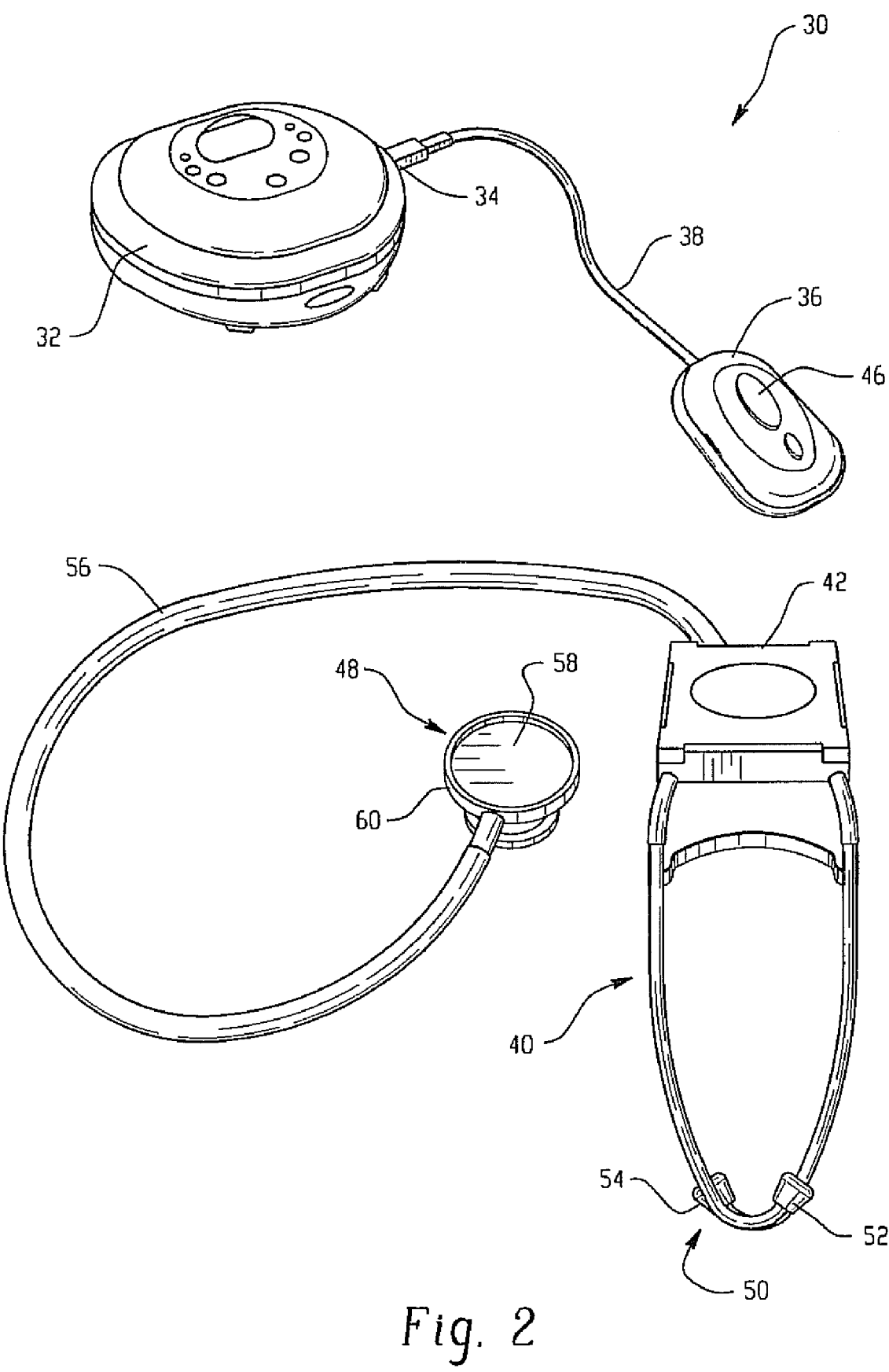
FIG. 2 an illustration of another embodiment of an exemplary arrangement for auscultation training.

FIG. 2 illustrates an embodiment of an exemplary arrangement for auscultation training. Arrangement 30 includes audio device 32 that is a species of device 12 described in relation to arrangement 10 of FIG. 1. Audio device 32 may include output 34, such as a headphone output jack, and FM radio transmitter 36 may attach to audio device 32 via wire 38 that plugs into output 34. FIG. 2's embodiment includes auscultation device 40 realized as a stethoscope and FM radio receiver 42 and speaker 44 (see FIG. 3) mounted to stethoscope 40.

FM radio transmitter 36 depicted in FIG. 2 may be similar to those used to transmit an audio signal from a portable compact disc player to an automobile stereo, as is known in the art. Any suitable FM radio transmitter (or other types of transmitters), however, may be used. Transmitter 36 may have the capability to broadcast on several frequencies and may include tuning dial 46 to change broadcast frequency. Additionally, transmitter 36 may have a tuning dial 46 to change broadcast frequency. Additionally, transmitter 36 may have a plurality of transmitters so that multiple audio signals may be transmitted at the same time at different frequencies to corresponding receivers tuned to the different frequencies within the same area. In an embodiment, transmitter 36 may be configured to operate only in a limited frequency range, such as for example about 88.1 MHz to about 8.7 MHz, which represents the industrial, scientific and medical (ISM) radio bands.

Stethoscope 40 is illustrated as an acoustic stethoscope but may be any suitable stethoscope, including all electronic stethoscope. Stethoscope 40 includes headpiece 48, which may be a headpiece assembly, earpiece assembly 50, which may include at least one piece, e.g., a pair of earpieces 52, 54, and tubing 56, which may be a tubing assembly, having a generally hollow interior. Tubing assembly 56 connects earpiece assembly 50 to headpiece assembly 48. Headpiece assembly 48 may include diaphragm 58 and body portion 60.

Figure 3:
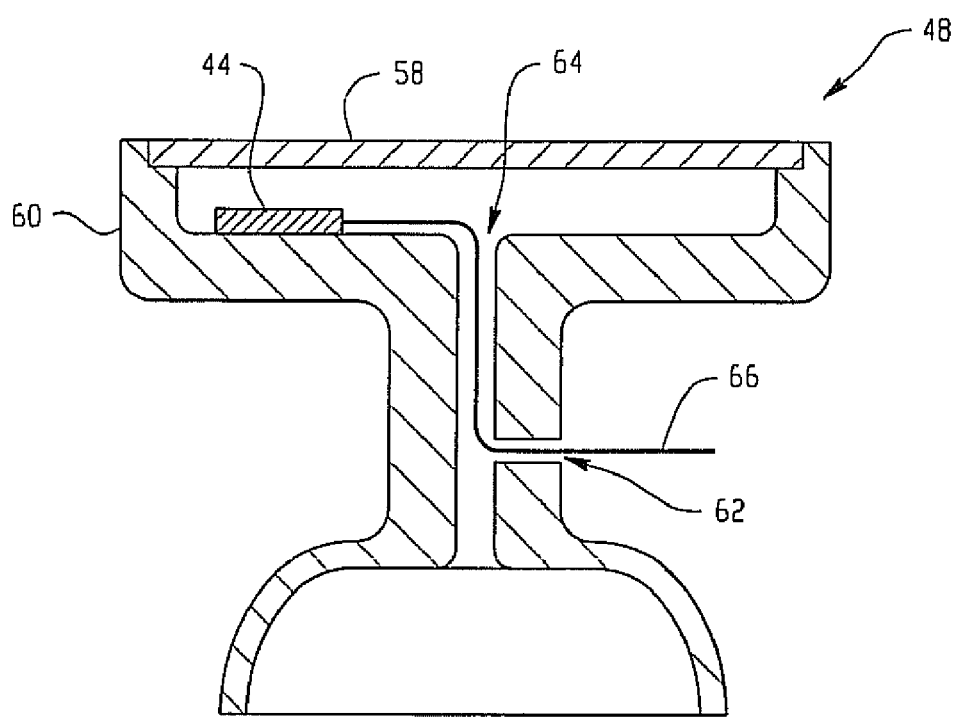
FIG. 3 is a cross section of an embodiment of an exemplary stethoscope head-piece assembly of the arrangement of FIG. 2.

Referring to FIG. 3, body portion 60 includes sound passageway 62 in communication with the hollow interior of tubing assembly 56. Diaphragm 58 mounts to body portion 60 adjacent but spaced apart from opening 64 for sound passageway 62. Speaker 44 may mount in the space between diaphragm 58 and body portion 60, proximate opening 64, such that speaker 44 is concealed within headpiece assembly 48 while readily communicating sound to passageway 62. In this manner, the sound generated by speaker 44 travels though stethoscope 40 in the same manner as sound generated by diaphragm 58 would, thus providing a realistic simulation of an auscultatory finding.

Receiver 42 and speaker 44 may be in circuit communication via electrical wire or lead 66. In an embodiment, radio receiver 42 may be all FM radio receiver that attaches to stethoscope 40 in any convenient location. For example, radio receiver 42 may attach to stethoscope 40 at approximately the location where tubing assembly 56 branches to each of ear pieces 52, 54. At this location, wire 66 may run from headpiece assembly 48 to receiver 42 inside of tubing assembly 56. In all embodiment, a small opening may be made in tubing assembly 56 to allow wire 66 to connect to receiver 42. Tubing assembly 56 may be sealed around wire 66 in any suitable manner. In additional embodiments, other FM radio receiver and speaker configurations are possible. As a non-limiting example, a small FM radio receiver chip and battery could mount between diaphragm 58 and body 60 proximate to speaker 44. Thus, receiver 42, speaker 44, and power source could all be concealed within headpiece assembly 48.

Arrangement 30 may include one or more power sources (not shown) in circuit communication with one or more of the devices of the arrangement, such as for example audio device 32, transmitter 36, receiver 42, and/or auscultation device 40. The one or more power sources may be, for example, one or more batteries enclosed within the devices. Of course, alternate means of providing power to the devices may be used, such as for example, using an external supply of alternating or direct current.

In operation in all auscultation training environment, audio device 32 of arrangement 30 depicted in FIG. 2, may be loaded with audio files of both normal and abnormal auscultatory findings. As a non-limiting example, if audio device 32 is a compact disc player, then a compact disc containing the audio files may be loaded into device 32. Or if audio device 32 is a digital audio player, digital audio files may be stored in the memory of device 32. The audio files may represent a wide variety of sounds. As a non-limiting example, the sounds may include, but are not limited to, heart sounds and murmurs, vascular sounds including bruits, lung sounds, abdominal sounds, and Korotkoff sounds.

Radio transmitter 36 may connect to audio device 32 via output 34 and radio receiver 42 located on stethoscope 40 may be tuned in to the transmitter frequency being used. A user may then use stethoscope 40 to examine a patient. If desired, the transmitter 36 and audio device 32 may be placed out of view of a user to provide all improved simulation environment for training and testing.

When a user places headpiece assembly 48 of stethoscope 40 in the proper location on the patient, an operator of audio devices 32 may play the appropriate audio file. The sound emitted by speaker 44 at least partially blocks out other normally heard sounds from the patient such that the user hears only the sound emitted by speaker 44 via stethoscope 40.

Because an embodiment provides for the sound being generated within stethoscope 40, different audio files may be selected and played based on certain variables. As a non-limiting example, appropriate heart sounds may be played and therefore heard by a user when headpiece assembly 48 is placed in different locations or when a simulated patient is in different positions. Vascular sounds such as bruits may be simulated in a similar manner.

Arrangement 30, therefore, provides embodiments for broadcasting simulated abnormal or normal medical sounds to a generally normal appearing stethoscope for the purpose of teaching or testing using simulated patient scenarios, while allowing for normal person-to-person interaction between the physician and simulated patient.

Because multiple frequencies can be used, an embodiment provides for two or more stethoscopes having different audio findings within the same room for simulation involving a group of clinicians. In such an embodiment, the range of transmitter 36 may be selected as appropriate. For example, transmitter 36 can be selected or adjusted to limit the effective range in order to allow multiple arrangements 30 to be used in the same general areas without interfering with each other.

Figure 4:
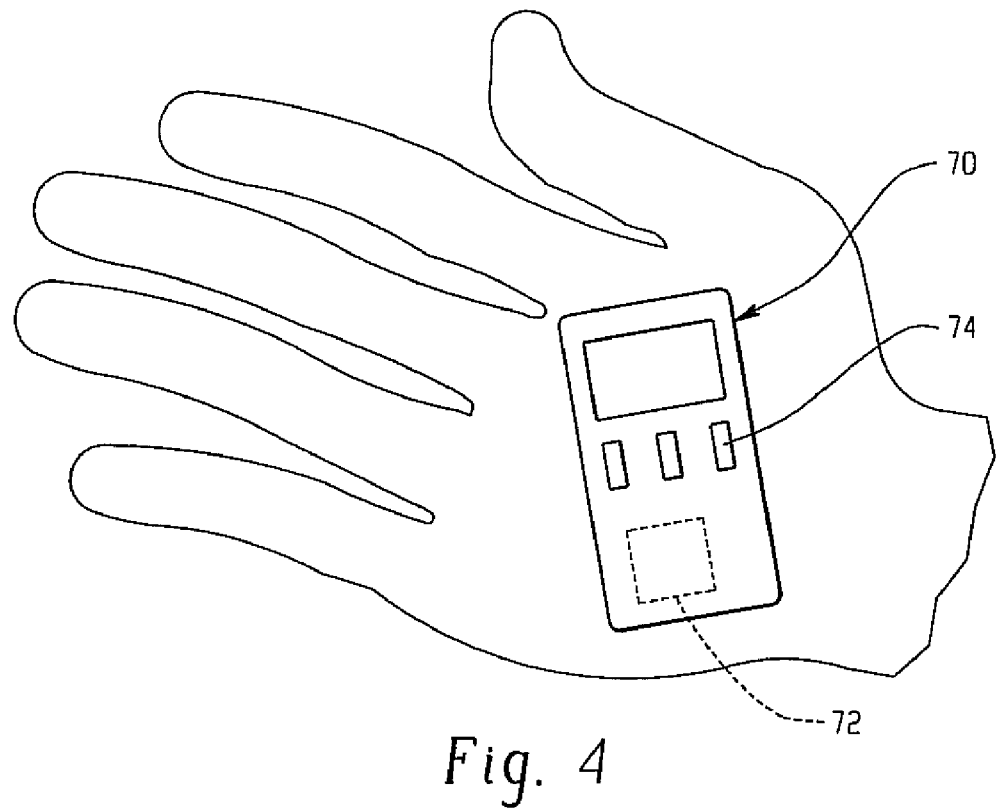
FIG. 4 is an illustration of an embodiment of an exemplary audio device and transmitter of the arrangements of FIGS. 1 and 2.

FIG. 4 illustrates another embodiment of an exemplary audio device and transmitter for use in arrangements of FIGS. 1 and 2. Audio device 70 may be realized as a compact digital audio player adapted to be concealed in the palm of a hand. Audio device 70 may include integrated FM transmitter chip 72 and one or more buttons 74 for operating device 70. Thus, audio device 70 may be operated by the patient being examined. This allows the patient to activate an appropriate audio file stored on audio device 70 for transmission when auscultation device 24 and the patient are properly positioned for detecting the sound represented by the audio file.

Figure 5:
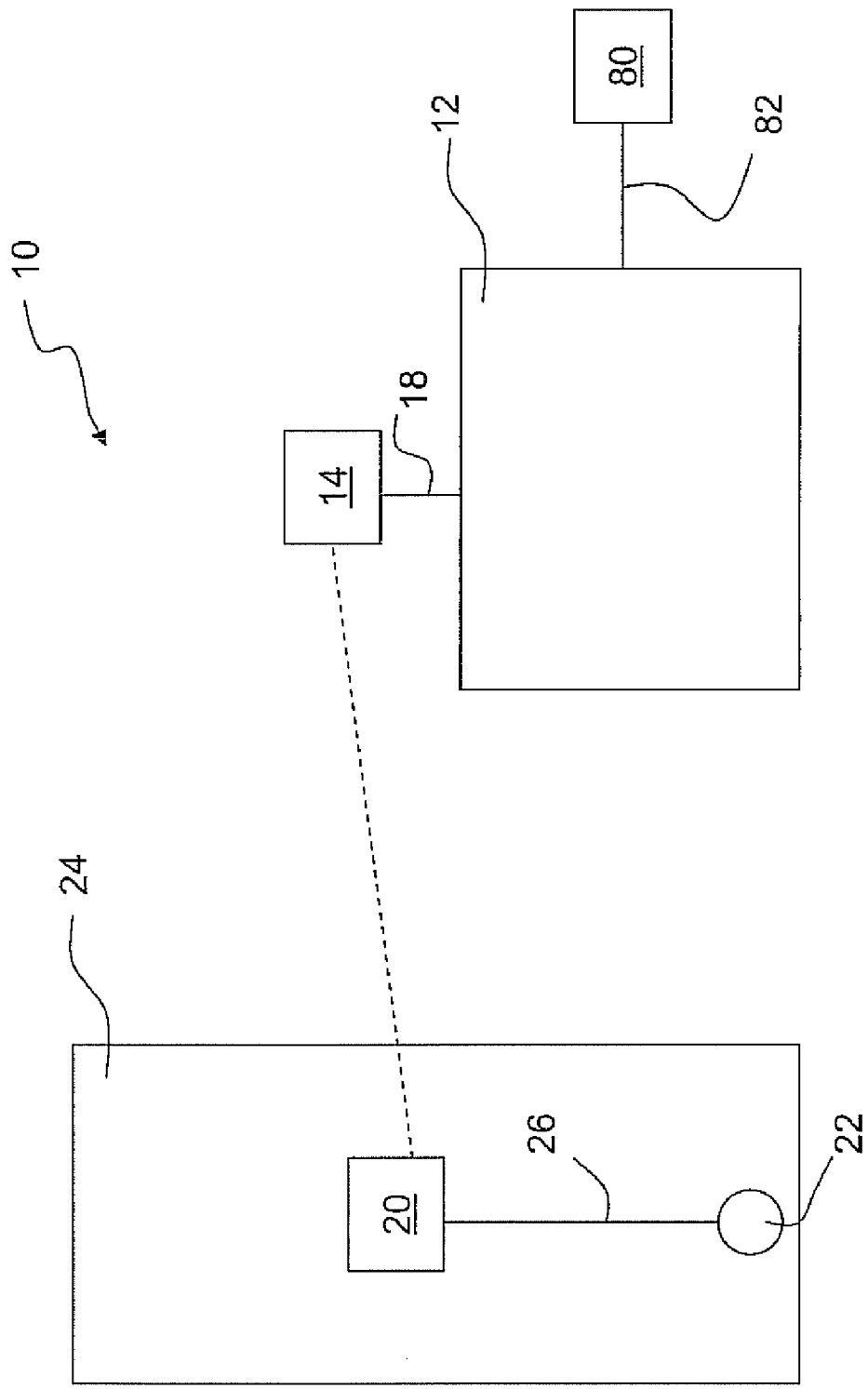
FIG. 5 is a schematic illustration of an embodiment of an exemplary arrangement for auscultation training.

FIG. 5 illustrates an embodiment of arrangement 10 that includes recording device 80 connected to audio-signal generating device 12 via electrical wire connection 82. This embodiment is similar to those embodiments relating to arrangement 10 discussed above, but this embodiment has recording device 80 that is capable of creating a record, electronic or other, of the signal generated from audio-signal generating device 12. In another embodiment, recording device 80 records not only the signal generated by audio-signal generating device 12, but recording device 80 also creates a record of the time and duration of the signal generated by audio-signal generating device 12.

Recording device 80 can be any known recording device that is capable of recording a signal generated by audio-signal generating device 12. Persons of ordinary skill in the art will be able to select useful recording devices without having to exercise undue experimentation.

In an embodiment, recording device 80 is connected to audio-signal generating device 12 via wire connection 82. But other embodiments connect recording device 82 and audio-signal generating device 12 via a wireless connection. Wireless technology is well known, and persons of ordinary skill in the art will be able to select and use useful wireless technology without having to exercise undue experimentation.

In still other embodiments of arrangement 10 that have recording device 80, recording device 80 is capable of and positioned in such a way that it can record signals either being emitted by, transferred by, or received by audio-signal generating device 12, electrical wiring connection 18, wireless transmitter 14, receiver 20, electrical wiring connection 26, audio output device 22, auscultation device 24, or a combination thereof. In any of these embodiments, a hard wire, wireless connection, or a combination thereof can be used to respectively connect recording device 80 to audio-signal generating device 12, electrical wiring connection 18, wireless transmitter 14, receiver 20, electrical wiring connection 26, audio output device 22, auscultation device 24, or a combination thereof.

Figure 6:
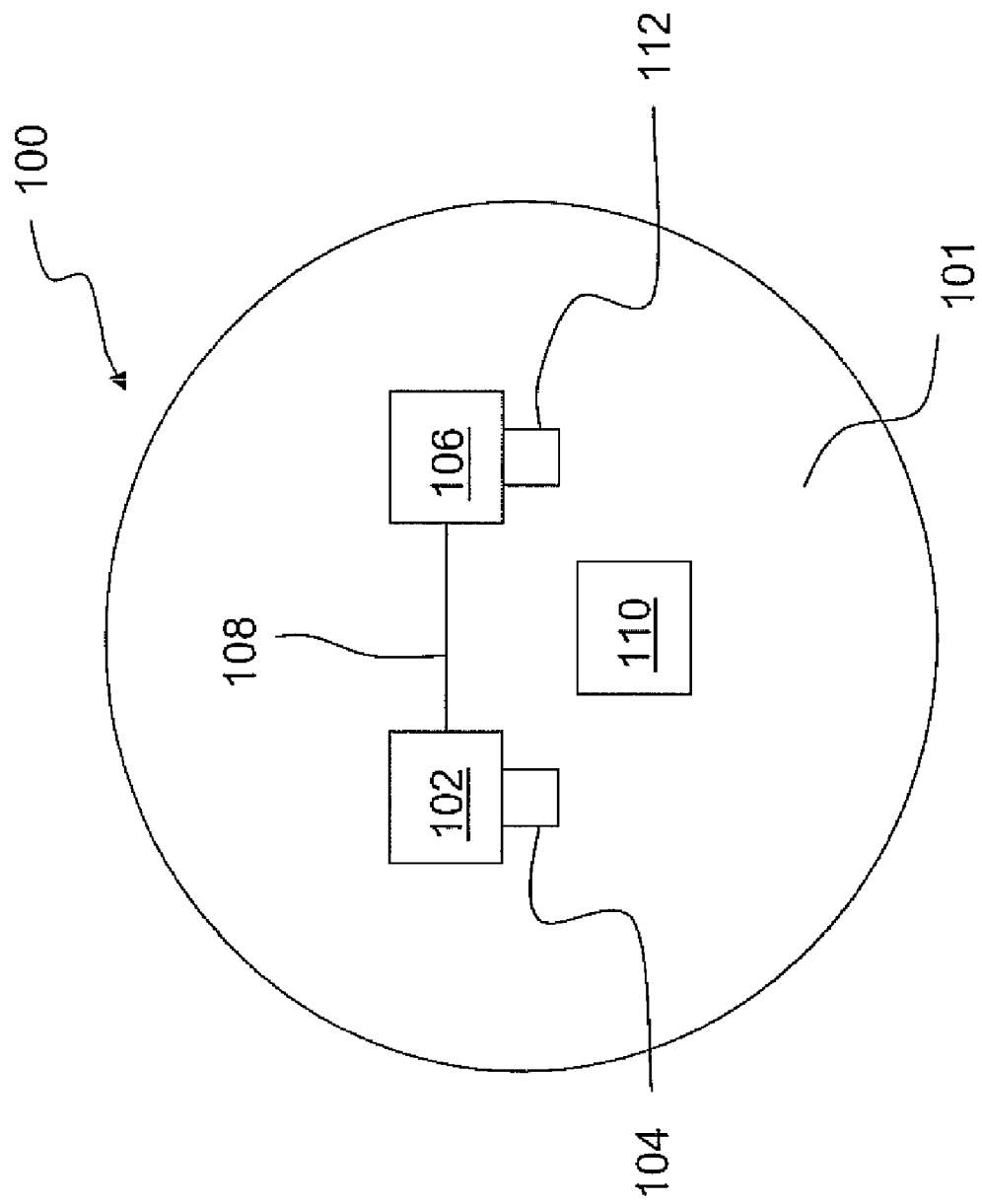
FIG. 6 is an illustrative auscultation training cap embodiment that can be used to retrofit a stethoscope.

FIG. 6 illustrates an embodiment generally directed to retrofitting a stethoscope, conventional or other, with cap 100 that can attach to the stethoscope headpiece. An embodiment provides for cap 100 having a design that includes a shape and characteristic dimensions that enable cap 100 to mechanically attach to a stethoscope headpiece. Specific embodiments are directed to cap 100 having cap body 101 that has a shape and characteristic dimensions that allow cap 100 to mechanically attach to a stethoscope headpiece by fitting cap body 101 at least partially over and around a portion of the stethoscope headpiece.

In other embodiments, cap body 101 does not have a shape and characteristic dimensions that allow it to mechanically attach to a stethoscope headpiece. In these embodiments, cap 100 can be attached to a stethoscope headpiece using any known technology for attaching a first mechanical element to a second mechanical element including any of the following non-limiting examples: adhesive, hook-and-loop fasteners, elastic band(s), and combinations thereof.

In still other embodiments, cap body 101 has a shape and characteristic dimensions that allow it to mechanically attach to a stethoscope headpiece, and cap 100 attaches to the stethoscope by fitting cap body 101 over and around a portion of the stethoscope headpiece in combination with using any known technology for attaching a first mechanical element to a second mechanical element including any of the following non-limiting examples: adhesive, hook-and-loop fasteners, elastic band(s), or a combination thereof.

Cap 100 or any of its components are not limited to being manufactured with any one particular material. Ali embodiment provides for cap body 101 being manufactured at least partially with a polymeric material, rubber material, or a combination thereof. The rubber or polymeric manufacturing material is useful in certain embodiments because it allows at least a portion of cap body 101 to stretch over and around a stethoscope headpiece. By cap body 101 stretching over and around the stethoscope headpiece, cap 100 mechanically attaches to the stethoscope headpiece.

In an embodiment, cap 100 has speaker 102, and speaker 102 is positioned either on the surface of or at least partially within cap 100 such that when cap 100 is mechanically attached to a stethoscope headpiece, sounds emitted from speaker 102 cause the stethoscope headpiece diaphragm to vibrate and thereby transmit the sound emitted by speaker 102 to the stethoscope user via the stethoscope tubing assembly. An embodiment provides for cap 100 mechanically attaching to a stethoscope headpiece such that at least a portion of cap 100 either covers or touches the stethoscope headpiece diaphragm. In all embodiment, cap 100 mechanically attaches to the stethoscope headpiece such that speaker 102 is either touching or in close proximity to the stethoscope headpiece diaphragm. Embodiments provide for speaker 102 having audio input jack 104. Audio input jack 104 can be used to input a sound signal into speaker 102.

An embodiment further provides for cap 100 having signal receiver 106 either positioned on the surface of or at least partially embedded therein. Signal receiver 106 can be connected to speaker 102 via electrical wire connection 108. In an alternative embodiment, signal receiver 106 is connected to speaker 102 via a wireless connection. Embodiments also provide for signal receiver 106 having input jack 112. Input jack 112 can be used to override all incoming wireless signal.

Another embodiment provides for cap 100 having recording device 110 either attached thereto or at least partially embedded therein. In this embodiment, recording device 110 can record the signal received by signal receiver 106, relayed or transmitted by electrical wiring connection 108, or emitted by speaker 102. Useful recording devices are well known, and can be selected by persons of ordinary skill in the art without having to exercise undue experimentation. Recording device 110 can create a record of the signal, the signal's time of transmission or emission, the duration of the signal, or any combination thereof. Recording device 110 can be connected to signal receiver 106, electrical wiring 108, speaker 102, or combinations thereof using hard wiring or wireless systems known to those skilled in the art.

A specific embodiment is directed to cap 100 having cap body 101, speaker 102, audio input jack 104, signal receiver 106, electrical wiring connection 108, recording device 110, and input jack 112. Additional embodiments are directed to cap 100 having any combination of these elements.

As a non-limiting example, any of the above embodiments directed to cap 100 can be used to train or educate a party selected from the group consisting of medical students, medical residents, attending medical physicians, and veterinary students, veterinary residents, veteran area physicians, nursing students, nurses, paramedic students, paramedics, respiratory therapy students, respiratory therapists, nurse practitioner students, nurse practitioners, physician assistant students, and physician assistants.

A non-limiting training embodiment uses a stethoscope retrofitted with one of the above embodiments relating to cap 100, to train or educate a party. As a non-limiting example, a training environment that simulates a real doctor-patient interaction is created by using either a mannequin or a human as a make-believe patient. The party being trained then uses the retrofitted stethoscope to examine the make-believe patient. During examination, the retrofitted stethoscope emits a sound or sounds, relating to a specific medical condition, which are relayed to the party being trained via the retrofitted stethoscope.

The embodiments have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

Having thus described the invention, it is now claimed:

1. A cap composition that can mechanically attach to a stethoscope headpiece, the cap composition comprising:
   a cap;
   a cap element having a design that includes a shape and characteristic dimensions that enable the cap to mechanically attach to a stethoscope headpiece;
   a speaker attached to and positioned on or at least partially within the cap, such that when the cap is attached to the stethoscope headpiece, the speaker is either touching or proximate to the stethoscope diaphragm such that a sound or signal emitted by the speaker can cause the stethoscope diaphragm to vibrate;
   a wireless signal receiver attached to the cap and in communication with the speaker, wherein the wireless signal receiver receives an audio signal representing at least one sound from a signal generator; and
   a recording device that makes a record of the sound or signal emitted by from the speaker.

2. The cap composition of claim 1, wherein the cap element is at least partially polymeric.

3. The cap composition of claim 1, wherein the cap element is at least partially rubber.

4. The cap composition of claim 1, wherein the shape and characteristic dimensions of the cap element allow the cap element to mechanically attach to a stethoscope headpiece by fitting over and around a portion of the stethoscope headpiece.

5. The cap composition of claim 4, wherein the cap element fits over and around the side portion of the stethoscope headpiece that houses the stethoscope diaphragm.

6. The cap composition of claim 1, wherein the speaker has a hard-wire audio-input jack.

7. The cap composition of claim 1, wherein the signal receiver has an input jack that can be used to override an incoming wireless signal.

8. The cap composition of claim 1, wherein the recording device further records the time and duration that the signal was emitted.

9. An arrangement for auscultation training, the arrangement comprising:
   a signal generator capable of generating an audio signal representing at least one sound;
   a transmitter that transmits the audio signal;
   an auscultation device remote from the transmitter, the auscultation device comprising:
     a receiver for receiving the audio signal transmitted by the transmitter;
     a speaker for communicating the audio signal received by the receiver; and
     a recording device that makes a record of the sound or signal emitted by from the speaker.

10. The arrangement of claim 9, wherein the recording device further records the time and duration of the signal that was emitted by the speaker.

11. The arrangement of claim 9, the auscultation device further comprises:
    a cap;
    a cap element having a design that includes a shape and characteristic dimensions that enable the cap to mechanically attach to a stethoscope headpiece; and wherein the speaker is attached to and positioned on or at least partially within the cap, such that when the cap is attached to the stethoscope headpiece, the speaker is either touching or proximate to the stethoscope diaphragm such that a sound or signal emitted by the speaker can cause the stethoscope diaphragm to vibrate.

12. The arrangement of claim 11, receiver is attached to the cap.

13. The arrangement of claim 12, wherein the signal receiver has an input jack that can be used to override an incoming wireless signal.

14. The arrangement of claim 11, wherein the shape and characteristic dimensions of the cap element allow the cap element to mechanically attach to a stethoscope headpiece by fitting over and around a portion of the stethoscope headpiece.

15. The arrangement of claim 14, wherein the cap element fits over and around the side portion of the stethoscope headpiece that houses the stethoscope diaphragm.

16. The arrangement of claim 11, wherein the speaker has a hard-wire audio-input jack, and wherein the transmitter and receiver are wireless.

\* \* \* \* \*

UNITED STATES PATENT AND TRADEMARK OFFICE
CERTIFICATE OF CORRECTION

PATENT NO. : 8,287,283 B2
APPLICATION NO. : 11/935468
DATED : October 16, 2012
INVENTOR(S) : Paul Jacques Charles Lecat It is certified that error appears in the above-identified patent and that said Letters Patent is hereby corrected as shown below:

In the Claims

Claim 1, col. 8, line 25: the portion reading "by from the speaker" should be amended to read "from the speaker."

Claim 9, col. 8, line 58: the portion reading "by from the speaker" should be amended to read "from the speaker."

Signed and Sealed this
Twelfth Day of May, 2015

Michelle K. Lee
*Director of the United States Patent and Trademark Office*